US012714777B2

(12) United States Patent
Smith et al.

(10) Patent No.: US 12,714,777 B2
(45) **Date of Patent: *Aug. 25, 2026**

(54) MEDICAL SYSTEMS, DEVICES, AND RELATED METHODS FOR WOUND THERAPY

(71) Applicant: Boston Scientific Scimed, Inc., Maple Grove, MN (US)

(72) Inventors: Paul Smith, Smithfield, RI (US); Scott Brechbiel, Burlington, MA (US); Jonathan Root, Townsend, MA (US); Rahul Prabhu, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 132 days.

This patent is subject to a terminal disclaimer.

(21) Appl. No.: 18/741,988

(22) Filed: Jun. 13, 2024

(65) Prior Publication Data

US 2024/0416025 A1 Dec. 19, 2024

Related U.S. Application Data

(60) Provisional application No. 63/508,017, filed on Jun. 14, 2023.

(51) Int. Cl.
*A61M 1/00* (2006.01)
*A61B 1/00* (2006.01)

(52) U.S. Cl.
CPC ......... *A61M 1/915* (2021.05); *A61B 1/00094* (2013.01); *A61B 1/00137* (2013.01)

(58) Field of Classification Search
CPC ........ A61M 1/915; A61M 1/84; A61M 1/916; A61M 2210/1042; A61M 1/912; A61M 1/87; A61B 1/00094; A61B 1/00137; A61B 2017/0034
See application file for complete search history.

(56) References Cited

U.S. PATENT DOCUMENTS 11,590,275 B2 2/2023 Hindmarsh et al.
2013/0331855 A1* 12/2013 Smith .................. A61B 17/221 606/114
2014/0276627 A1 9/2014 Jenkins et al.
(Continued)

FOREIGN PATENT DOCUMENTS

WO 2022/157513 A2 7/2022

*Primary Examiner* — John R Schnurr
(74) *Attorney, Agent, or Firm* — Bookoff McAndrews PLLC

(57) ABSTRACT

A medical system that includes a handle, a shaft extending distally from the handle, the shaft including one or more channels extending between the handle and a distal end of the shaft, and a cap assembly coupled to the distal end of the shaft. At least one of the one or more channels includes a working channel. The cap assembly includes an opening that is positioned in alignment with at least one of the one or more channels at the distal end of the shaft. The medical system includes a chamber that extends distally from the opening and a porous body movably disposed within the chamber. The chamber is positioned in alignment with the working channel, and the porous body is configured to transition from a compressed configuration when disposed inside the chamber to an expanded configuration upon extending outwardly from the chamber.

18 Claims, 8 Drawing Sheets

(56) References Cited

U.S. PATENT DOCUMENTS

| | | | | |
|---|---|---|---|---|
| 2019/0117857 | A1* | 4/2019 | Hindmarsh | A61M 27/00 |
| 2021/0260335 | A1* | 8/2021 | Burke | A61M 25/0023 |
| 2023/0012427 | A1 | 1/2023 | Loske | |

* cited by examiner 200
212
220
213
208
119
210
211
203
102
202

220
212
213
200
208
119
210
211
203
102
202

220
200
212
208
119
210
211
203
102
202

220
230

212
215
213
200
208
119
210
211
203
102
202

MEDICAL SYSTEMS, DEVICES, AND RELATED METHODS FOR WOUND THERAPY

CROSS-REFERENCE TO RELATED APPLICATIONS

This application claims the benefit of priority of U.S. Provisional Patent Application No. 63/508,017, filed on Jun. 14, 2023, the entirety of which is incorporated herein by reference.

TECHNICAL FIELD

Various aspects of the disclosure generally relate to medical systems, devices, and related methods that may be used to treat a subject. In particular, aspects of the disclosure relate to medical systems, devices, and methods for wound therapy, such as endoscopic vacuum therapy that includes applying negative air pressure to tissue for wound therapy.

BACKGROUND

Endoscopic and open surgical procedures of the gastrointestinal (GI) tract include, for example, colonic resection, bariatric surgery, esophagectomy, gastric bypass, and sleeve gastrectomy, among others. These procedures may result in perforation, post-surgical leaks, or other wounds of the GI tract. Limited treatment options exist for managing such wounds, which have significant morbidity and mortality rates. Options include surgical re-operation and endoscopic placement of a stent or one or more clips. Surgery is invasive and involves high morbidity and mortality rates. Although endoscopic stent placement is less invasive, the placed stent can migrate from the intended location and/or wall off an infection at the treatment site, which may exacerbate the infection and/or inhibit drainage. The systems, devices, and methods of the current disclosure may rectify one or more of the deficiencies described above or address other aspects of the art.

SUMMARY

Each of the aspects disclosed herein may include one or more of the features described in connection with any of the other disclosed aspects.

Aspects of the disclosure relate to, among other things, systems, devices, and methods for treating a subject. Aspects of this disclosure relate to medical systems, devices, and methods for wound therapy, such as endoscopic vacuum therapy that includes applying negative air pressure to tissue for wound therapy.

According to an example, a medical system includes a handle; a shaft extending distally from the handle, the shaft including one or more channels extending between the handle and a distal end of the shaft, wherein at least one of the one or more channels includes a working channel; a cap assembly coupled to the distal end of the shaft, the cap assembly including an opening that is positioned in alignment with at least one of the one or more channels at the distal end of the shaft, and a chamber that extends distally from the opening, wherein the chamber is positioned in alignment with the working channel; and a porous body movably disposed within the chamber, the porous body is configured to transition from a compressed configuration when disposed inside the chamber to an expanded configuration upon extending outwardly from the chamber.

Any of the medical systems described herein may include any of the following features. A tube movably coupled to the cap assembly, the tube is configured to move between a first position and a second position relative to the cap assembly to transition the porous body between the compressed configuration and the expanded configuration. In the first position, a distal end of the tube is positioned outside the chamber such that the porous body is maintained inside the chamber and in the compressed configuration; and wherein, in the second position, the distal end of the tube is positioned inside the chamber such that the porous body is extended outside of the chamber and transitioned to the expanded configuration. The tube is a vacuum tube that is coupled to a negative pressure source at a proximal portion of the vacuum tube, and to the porous body at a distal portion of the vacuum tube. The vacuum tube is configured to apply negative pressure to the porous body as provided by the negative pressure source. The chamber is configured to receive the tube when the tube is in the second position, and at least a portion of the chamber is deformable to facilitate releasing the tube from the chamber. The tube is slidably received within the working channel of the shaft. The cap assembly is removably mounted on an exterior surface of the distal end of the shaft. The cap assembly is selectively rotatable about the exterior surface of the distal end of the shaft such that the chamber is repositionable relative to the one or more channels while maintaining alignment with the working channel. The porous body is a sponge, a gauze, a film, or a membrane. The chamber is at least partially transparent such that the porous body disposed inside the chamber is visible through the chamber. The chamber includes a window such that the porous body disposed inside the chamber is visible through the window by an imaging device. The chamber includes an extended wall that defines a cross-sectional dimension of the chamber that minimizes compression of the porous body received within the chamber. The extended wall is sized and shaped such that the chamber has a tear drop configuration. The cap assembly is securely attached to the shaft via a frictional engagement between a body of the cap assembly and a distal tip of the shaft.

According to another example, a medical device includes a cap assembly configured to be attached about a shaft of an endoscope such that a working channel of the endoscope is accessible through an opening of the cap assembly at a distal end of the shaft, the cap assembly including a chamber that extends distally from the distal end and is disposed in alignment with a working channel of the shaft; and a porous body received within the chamber, the chamber configured to compress the porous body relative to the shaft; wherein the porous body is movable relative to the cap assembly from a first position inside the chamber and in a compressed configuration to a second position outside of the chamber and in an expanded configuration.

Any of the medical devices described herein may include any of the following features. A tube disposed inside the working channel, the tube is coupled to a negative pressure source at a first end and to the porous body at a second end, such that the negative pressure source is in fluid communication with the porous body via the tube; wherein the tube is movable relative to the working channel to extend the porous body out from the chamber, and configured to generate a vacuum through the porous body in response to activating the negative pressure source. The chamber is configured to receive the tube when the tube extends the porous body out from the chamber, and at least a portion of the chamber is deformable to facilitate releasing the tube from the chamber. The chamber includes an extended wall that defines a cross-sectional dimension of the chamber that minimizes compression of the porous body received within the chamber; wherein the extended wall is sized and shaped such that the chamber has a tear drop configuration.

According to another example, a method for treating a wound cavity with a medical device includes positioning a shaft of the medical device at the wound cavity, wherein a cap assembly is mounted onto the shaft such that the cap assembly is positioned adjacent to the wound cavity, wherein a chamber of the cap assembly is disposed in alignment with a working channel of the shaft; extending a porous body out from within the chamber in response to moving a tube relative to the working channel, such that the porous body expands upon exiting the chamber and entering the wound cavity, wherein the tube is coupled to the porous body and in fluid communication with a negative pressure source; and applying a negative pressure at the wound cavity via the porous body in response to activating the negative pressure source.

It may be understood that both the foregoing general description and the following detailed description are exemplary and explanatory only and are not restrictive of the invention, as claimed. As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "diameter" may refer to a width where an element is not circular. The term "distal" refers to a direction away from a user/toward a treatment site, and the term "proximal" refers to a direction toward a user. The terms "downward," "upward," "lower," "upper," "bottom," and "top" may refer to directions relative to the views of the elements shown throughout the drawings. The term "exemplary" is used in the sense of "example," rather than "ideal." The term "approximately," or like terms (e.g., "substantially"), includes values+/−10% of a stated value.

BRIEF DESCRIPTION OF THE DRAWINGS

The accompanying drawings, which are incorporated in and constitute a part of this specification, illustrate aspects of this disclosure and together with the description, serve to explain the principles of the disclosure.

DETAILED DESCRIPTION

Endoluminal vacuum therapy (EVAC) is an adaptation of negative pressure wound therapy (i.e., vacuum therapy or wound vac), which may be used for external treatment of chronic, non-healing wounds, where a vacuum-sealed material (e.g., a sponge) is inserted into the wound and a negative pressure is applied to the sponge to promote drainage. In a typical EVAC procedure, negative pressure is delivered to a wound site internally within the GI tract, for example through a nasogastric tube having a sponge at its terminal end. The sponge may be placed endoscopically into a perforation, leak, or other wound, and negative pressure may then be applied to promote drainage from the wound.

Embodiments of this disclosure include devices, systems, and methods specifically for EVAC procedures. In some embodiments, EVAC may include endoluminal placement of a porous body (e.g., a sponge or other like material) into a wound site, for example a perforation, a cyst, a leak, or an anastomosis. The porous body may be placed within a wound via a catheter, scope (e.g., endoscope, bronchoscope, colonoscope, etc.), tube, or sheath, which may be inserted into the GI tract via a natural orifice. The orifice may be, for example, the nose, mouth, or anus, and a distal end of the catheter, scope, tube, or sheath (and thus the porous body) may be positioned in any portion of the GI tract, including the esophagus, stomach, duodenum, large intestine, or small intestine.

Figure 1:
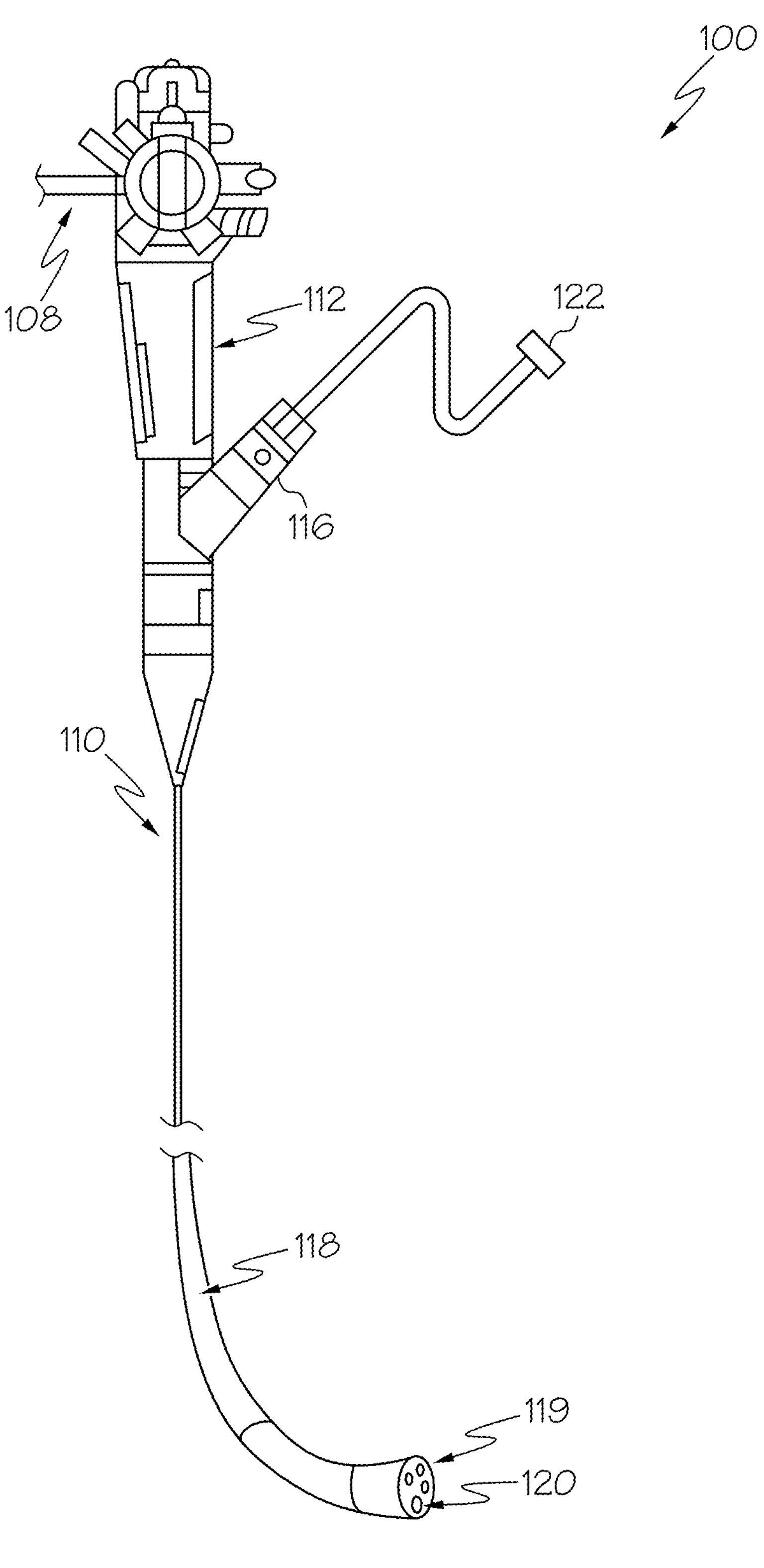
FIG. 1 shows a perspective view of an exemplary medical system, according to some embodiments.

FIG. 1 depicts an exemplary medical system 100. Medical system 100 may include an insertion device, such as an endoscope, which may be inserted into an esophagus of a patient. Medical system 100 may include a handle 112 and a shaft 110 extending distally from handle 112. Shaft 110 may include one or more channels extending therethrough from a proximal portion positioned adjacent to handle 112 and a distal portion 118 terminating at a distal tip 119. In some embodiments, medical system 100 may include an umbilicus (not shown), which may connect a port 108 of the endoscope to sources of, for example, air, water, suction, power, image processing and/or viewing equipment. In some embodiments, medical system 100 may include an imaging element and/or a lighting element, such as at distal tip 119, to aid in accurately positioning shaft 110 adjacent a target treatment site (e.g., a wound cavity) during an EVAC procedure. Using one or more of the channels of shaft 110, a user of medical system 100 may deploy or otherwise deliver a medical tool or instrument to the target treatment site, such as a medical tool 122 received through a port 116 on handle 112.

In some aspects, handle 112 may include one or more actuators along a proximal end of handle 112 (e.g., adjacent to port 108), for example, to control the movement of shaft 110, and particularly distal portion 118, the activation of one or more imaging element(s) and lighting element(s), and control a deflection, position, or orientation of distal tip 119. It is noted that FIG. 1 illustrates distal tip 119 of medical system 100 (e.g., an endoscope) as being "forward-facing" in that the features of distal tip 119, such as the one or more channels of shaft 110, may face distally (i.e., forward of a distalmost face of distal tip 119). It should be appreciated that this disclosure also encompasses other configurations of distal tip 119, including distal tip 119 being "side-facing" in which the one or more channels of shaft 110 may be disposed on a radially outer side of distal tip 119 so that they point in a radially outward direction, approximately perpendicularly to a longitudinal axis of distal portion 118.

Still referring to FIG. 1, although insertion device or medical system 100 is discussed above as being an endoscope, this disclosure is not so limited. Although the disclosure may refer at different points to an endoscope, it will be appreciated that, unless otherwise specified, duodenoscopes, endoscopes, gastroscopes, endoscopic ultrasonography ("EUS") scopes, colonoscopes, ureteroscopes, bronchoscopes, laparoscopes, cytoscopes, aspiration scopes, sheaths, catheters, or any other suitable delivery device or insertion device may be used in connection with the systems, devices, elements, assemblies, methods, etc. described herein.

Figure 2:
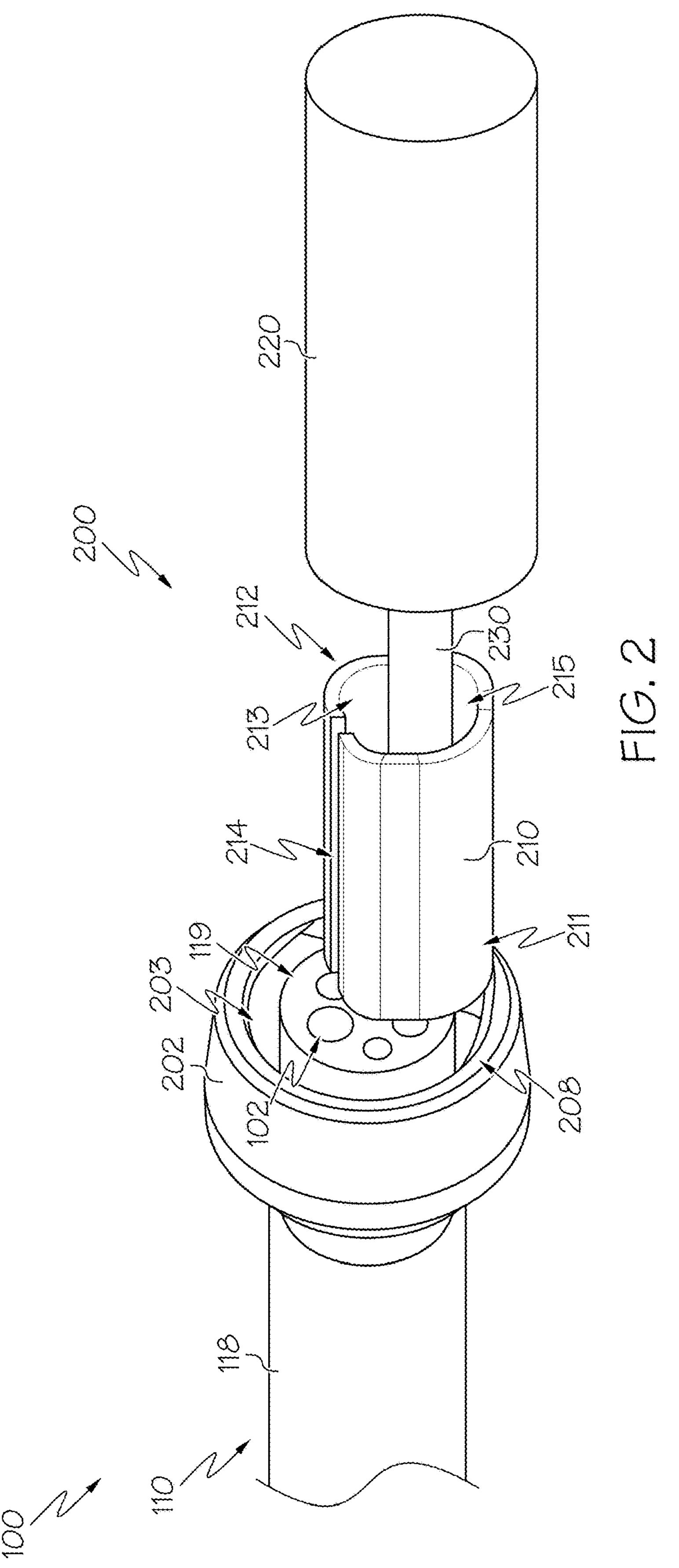
FIG. 2 shows a perspective view of an exemplary medical device coupled to the medical system of FIG. 1, according to some embodiments.

Referring now to FIG. 2, medical system 100 may include a medical device coupled to shaft 110. In the example, the medical device may include a cap assembly 200 that may be removably coupled to shaft 110 along distal portion 118. In other words, cap assembly 200 may be removably mounted onto distal portion 118. Cap assembly 200 may be configured to attach to an exterior surface of shaft 110 adjacent to distal tip 119 via various suitable means. In one example, cap assembly 200 may form a frictional engagement with the exterior surface of shaft 110, thereby securely attaching cap assembly 200 to shaft 110. In embodiments in which shaft 110 includes an articulating section, it should be appreciated that cap assembly 200 may be coupled to shaft 110 distally relative to the articulating section. For example, an entirety of cap assembly 200 may be distal to a distalmost end of the articulation section.

Cap assembly 200 may include a body 202 having a cylindrical configuration that is sized, shaped, and/or otherwise configured to receive shaft 110. In other words, body 202 may define a channel 203 extending through cap assembly 200, with body 202 being configured to receive shaft 110 through channel 203 such that body 202 may extend about the exterior surface of shaft 110, and particularly from distal portion 118, when shaft 110 is received therethrough. Cap assembly 200 may be configured such that an interior surface of body 202 that defines channel 203 may frictionally engage distal portion 118 of shaft 110 to inhibit movement (e.g., axial translation) of distal tip 119 received therein. Accordingly, body 202 may be configured to engage and/or grasp an exterior of distal portion 118 when distal portion 118 is received through body 202, thereby coupling cap assembly 200 to shaft 110. Body 202 may define an opening 208 for receiving distal tip 119 of shaft 110 when distal portion 118 is received through channel 203 of body 202.

Cap assembly 200 may further include a chamber 210 extending distally from body 202. Chamber 210 may have a longitudinal length defined between a first (proximal) end 211 that is integrally formed with body 202, and a second (distal) end 212 positioned opposite first end 211. In the example, chamber 210 may have a substantially rigid configuration. For example, chamber 210 may be formed of a thermoplastic polymer, a semi-rigid plastic, etc. In other examples, chamber 210 may include a pocket, a bag, or other suitable components with a relatively flexible configuration.

Still referring to FIG. 2, chamber 210 may define an interior lumen 215 that is sized, shaped, and/or otherwise configured to receive one or more vacuum therapy devices therein. For example, the vacuum therapy device may include a device that is configured to interface with a target treatment site (e.g., tissue) within a subject (e.g., a patient). The vacuum therapy device may be at least partially absorbent and include, but is not limited to, a vacuum therapy sponge, a gauze, a film, a membrane, and more. In the example, the vacuum therapy device may include a porous body 220. In some embodiments, porous body 220 may include any suitable biocompatible material that may absorb liquids and/or permit liquid to pass therethrough via negative pressure. The material may be flexible, compressible, porous, hydrophilic, sterile, and/or disposable. The material of porous body 220 may be or may include an open-cell foam. Suitable materials may include polyurethanes, polymers with ester and/or ether functional groups, composite materials, and any other medical-grade material or materials.

Porous body 220 may have a longitudinal length and a lateral diameter and/or width that are at least partially flexible. As such, porous body 220 may be at least partially compressible such that chamber 210 may be configured to compress porous body 220 to a compressed configuration when received therein. Chamber 210 may be further configured to fix porous body 220 therein absent an application of force applied to porous body 220 for deployment from chamber 210.

It should be appreciated that a diameter of porous body 220 may correspond to a diameter of interior lumen 215 of chamber 210 when porous body 220 is in the compressed configuration. For example, the diameter of interior lumen 215 may be less than about 20 millimeters to facilitate navigation of cap assembly 200 through a tortuous pathway of the subject (e.g., a patient), such as an esophagus. As described further herein, cap assembly 200 may be configured to transition porous body 220 from the compressed configuration to an expanded configuration upon deploying porous body 220 distally from interior lumen 215 of chamber 210 (see FIGS. 5B-5D).

Chamber 210 may include a distal opening 213 at second end 212 that is sized and/or shaped to facilitate deployment of porous body 220 from within chamber 210. Chamber 210 may further include a window 214 extending along the longitudinal length of chamber 210, and particularly between first end 211 and second end 212. Window 214 may be, for example, a slot. With porous body 220 received within chamber 210, cap assembly 200 may be operable to facilitate visualization of porous body 220 from an exterior of chamber 210 via window 214. In other words, cap assembly 200 may be operable to provide visual feedback of a location of porous body 220 during a procedure of delivering porous body 220 to a target treatment site (e.g., a wound cavity) via medical system 100 and cap assembly 200 through window 214. For example, chamber 210 may be positioned relative to distal tip 119 such that an imaging assembly 102 of medical system 100 may be operable to visualize porous body 220 through window 214. In other examples, window 214 may be omitted entirely. In some embodiments, chamber 210 may be formed of an opaque material. In other embodiments, at least a portion of chamber 210 may be transparent and/or semi-transparent to further facilitate visual inspection of porous body 220 from within chamber 210. In this instance, porous body 220 may be visible through chamber 210.

Still referring to FIG. 2, cap assembly 200 may include a fluidics component that is coupled to, and in fluid communication with, porous body 220. For example, the fluidics component of cap assembly 200 may include a tube member 230 (e.g., a vacuum tube) that is coupled to a proximal end of porous body 220. Tube member 230 may be formed from a polymer or any other suitable biocompatible material. In some embodiments, tube member 230 may include a shape memory membrane, for example a Nitinol membrane, or may be formed of a shape memory and/or heat-set material (e.g., Nitinol). As described herein, tube member 230 may be configured to move porous body 220 in response to movement of tube member 230 relative to body 202 and shaft 110.

Figure 3:
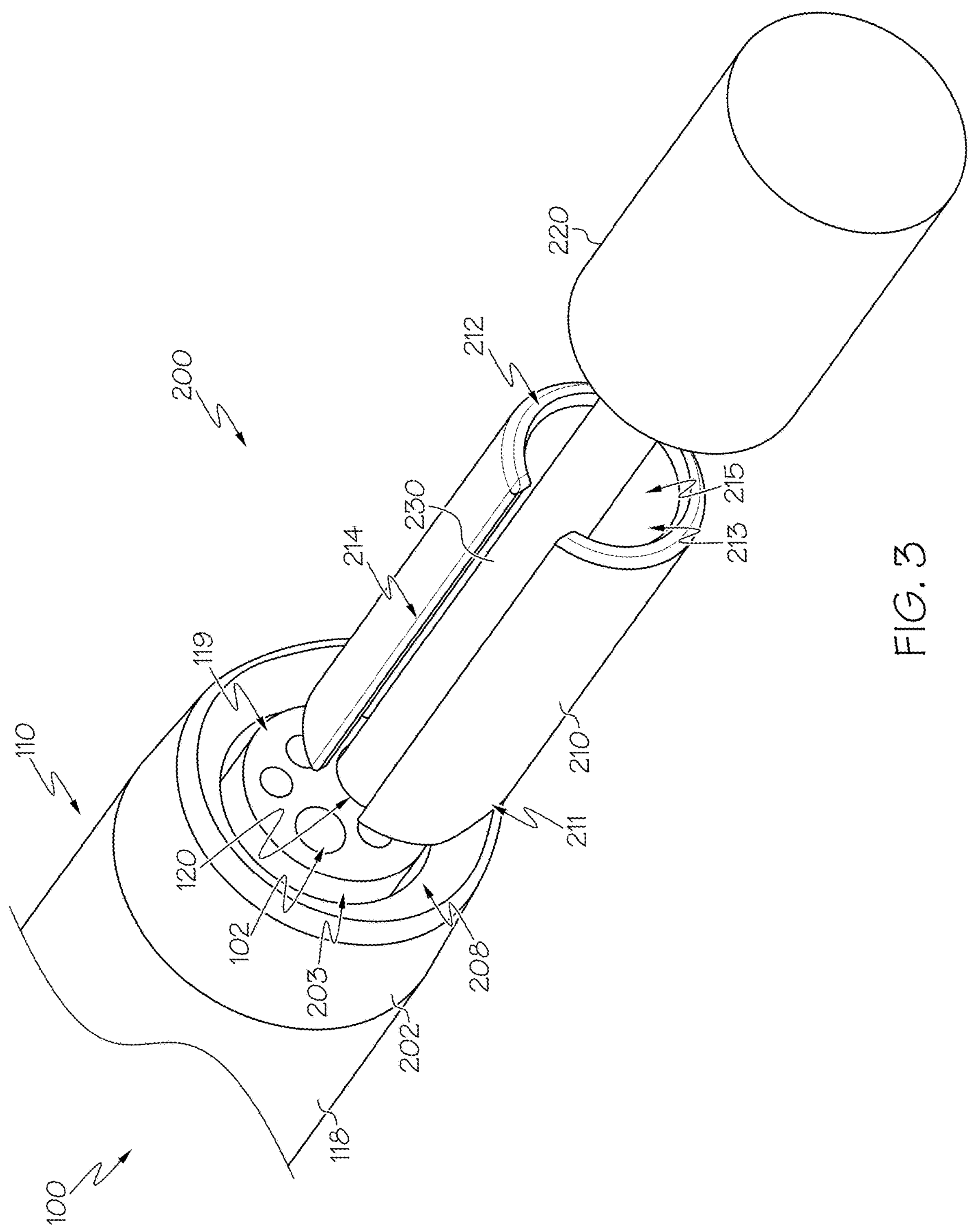
FIG. 3 shows a perspective view of the medical device of FIG. 2, according to some embodiments.

As best seen in FIG. 3, tube member 230 may be positioned inside shaft 110, and particularly tube member 230 may be slidably received within a working channel 120 of shaft 110. Tube member 230 may extend out of working channel 120 at distal tip 119 and into chamber 210 via opening 208. When porous body 220 is disposed within chamber 210, the proximal end of porous body 220 may be positioned adjacent to body 202 and first end 211, such that a terminal (distal) end of tube member 230 may similarly be positioned within body 202 and disposed inside working channel 120. Tube member 230 may be configured to move (e.g., translate) porous body 220 relative to chamber 210, such as in a distal direction through distal opening 213 to extend at least a distal portion of porous body 220 distally outwardly from chamber 210, in response to tube member 230 moving distally relative to body 202 (see FIGS. 4B-4D). In this instance, tube member 230 may extend out of working channel 120, into chamber 210, and distally relative to first end 211, as shown in FIG. 4 (showing porous body 220 being partially deployed from chamber 210 and partially retained within chamber 210).

Although not shown, it should be understood that tube member 230 may include one or more openings and/or ports at a distal end of tube member 230, such that the one or more openings and/or ports are fluidly coupled to porous body 220. As described herein, tube member 230 may be fluidly coupled to a negative pressure (vacuum) source at a proximal end of tube member 230 (not shown) that is opposite of the distal end of tube member 230. Accordingly, porous body 220 may be in fluid communication with the negative pressure source via tube member 230, and particularly through the one or more openings and/or ports at the distal end of tube member 230.

Figure 4:
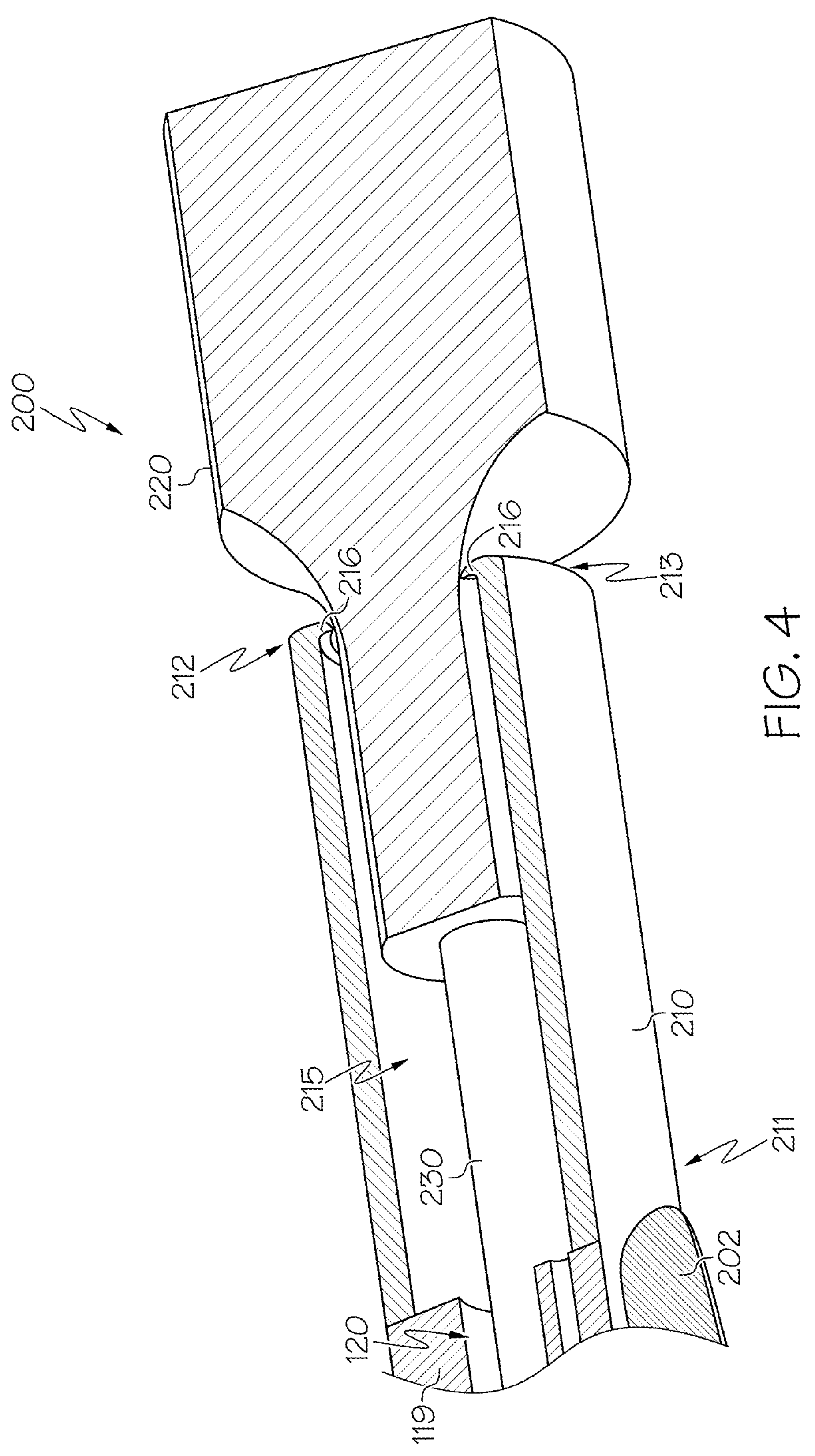
FIG. 4 shows a cross-sectional view of the medical device of FIG. 2, according to some embodiments.

Still referring to FIGS. 3-4, body 202 may be sized, shaped, and/or otherwise configured to position chamber 210 in relative axial alignment with the one or more channels of shaft 110, and particularly working channel 120, when cap assembly 200 is coupled to distal portion 118. Stated differently, chamber 210 may be arranged relative to body 202 such that chamber 210 is suspended in axial alignment with an opening of the one or more channels of shaft 110, including at least working channel 120, when body 202 is coupled to distal portion 118. In this instance, an opening of working channel 120 (and one or more of the other channels of shaft 110) may coincide with chamber 210 such that tube member 230 extending through working channel 120 may be received in chamber 210. At least one or more openings of the other channels of shaft 110 may be positioned in alignment with opening 208 and outside (e.g., radially outward) of chamber 210, such that one or more medical tools or instruments (e.g., air, water, light, etc.) may extend through said channels and out of shaft 110 for accessing the target treatment site via opening 208, without interference from chamber 210.

Referring specifically to FIG. 4, cap assembly 200 may include a retention mechanism 216 along chamber 210 for retaining porous body 220 therein absent an application of distal force applied thereto for deploying porous body 220 from chamber 210. In some embodiments, retention mechanism 216 may include various suitable devices, such as a protrusion, a tab, an abutment, a clip, and more. In the example, retention mechanism 216 may include a beveled edge disposed about distal opening 213 at second end 212. The beveled edge of retention mechanism 216 may be sized, shaped, and/or otherwise configured to extend laterally inward from second end 212 and at least partially into distal opening 213.

Retention mechanism 216 may be configured to abut against a distalmost end of porous body 220 when porous body 220 is disposed within interior lumen 215 of chamber 210, to inhibit inadvertent misplacement/misdeployment of porous body 220 from chamber 210. Retention mechanism 216 may be configured to permit distal deployment of porous body 220 from chamber 210 in response to an application of distal force onto porous body 220, such as from tube member 230. It should be appreciated that the distal force may exceed a predetermined threshold to advance porous body 220 beyond retention mechanism 216 and out of chamber 210. Upon exiting chamber 210, portions of porous body 220 may gradually transition to the expanded configuration, as shown in FIG. 4.

In exemplary use, as shown in FIGS. 5A-5D, medical system 100 may be utilized to perform endoluminal vacuum therapy to treat a target treatment site by deploying a vacuum therapy device (e.g., porous body 220) via cap assembly 200. For example, medical system 100 may be operated such that shaft 110 is navigated through a subject (e.g., a patient), such as within the subject's GI tract, until arriving at the target treatment site (e.g., a wound cavity). The wound cavity may be in the form of an anastomotic leak, a perforation, or other injury within the GI tract. Distal tip 119, with cap assembly 200 coupled thereto, may be positioned adjacent to the wound cavity. A location of porous body 220 may be determined based on the visual feedback generated by cap assembly 200 by visualizing the position of porous body 220 through window 214 by imaging assembly 102 while porous body 220 remains disposed inside chamber 210.

Figures 5A, 5B:
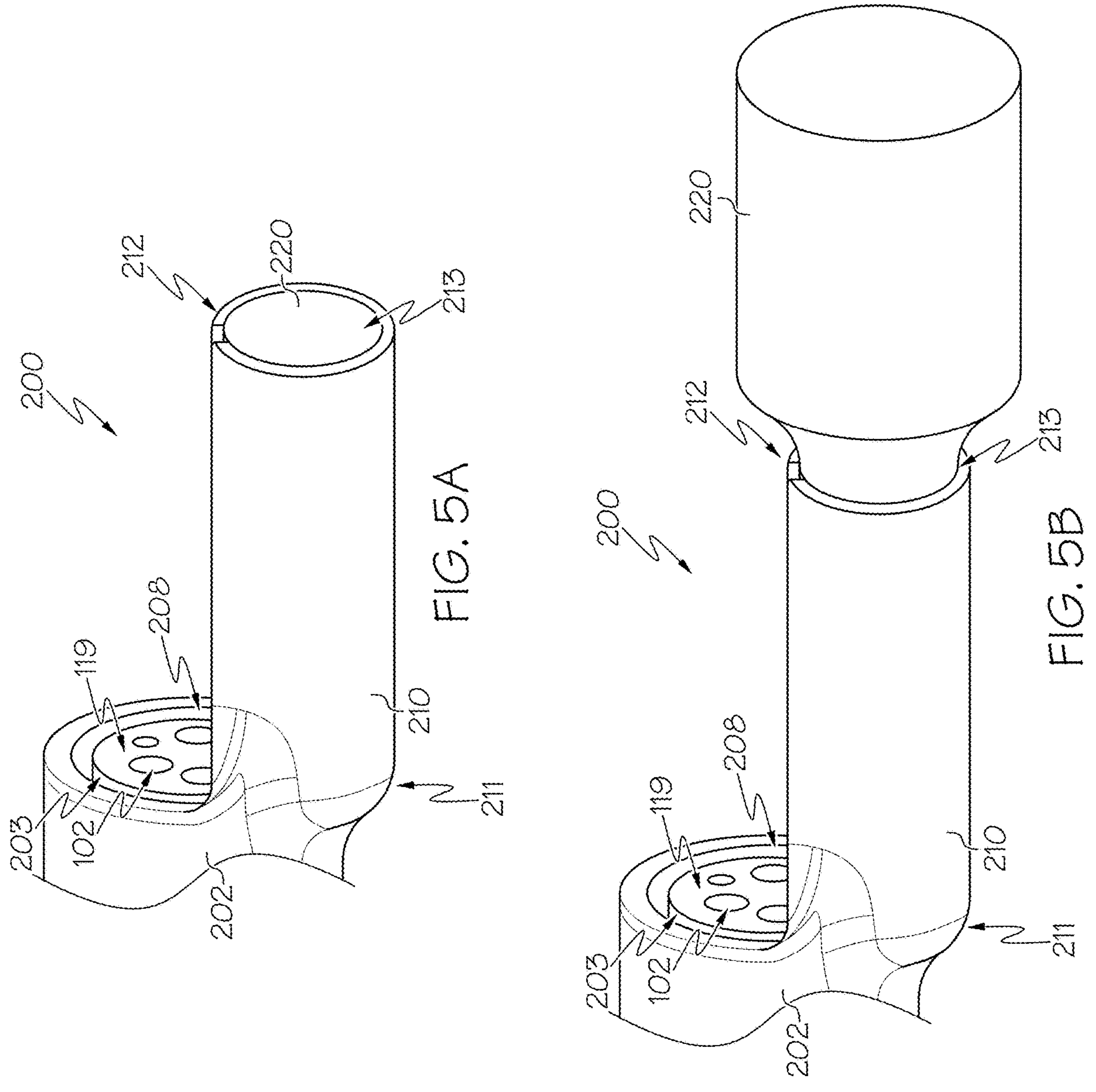
FIG. 5A shows a perspective view of the medical device of FIG. 2 in a first position, according to some embodiments.
FIG. 5B shows a perspective view of the medical device of FIG. 2 in a second position, according to some embodiments.

Referring specifically to FIG. 5A, distal tip 119 may be arranged to position chamber 210 towards the wound cavity. In this instance, porous body 220 may access the wound cavity, in addition to any medical tools or instruments disposed in the one or more channels of shaft 110 which are accessible through cap assembly 200 via opening 208. In this instance, tube member 230 may be in a first position relative to working channel 120 with porous body 220 disposed entirely within chamber 210. It should be appreciated that the first position of tube member 230 is a proximalmost position in which tube member 230 is disposed within working channel 120 and positioned outside of (i.e., proximally of) chamber 210. In the first position, a distal end of tube member 230 may be positioned outside of chamber 210. In other embodiments, porous body 220 may have a longitudinal length that is smaller than a longitudinal length of chamber 210. In this instance when in the first position, the distal end of tube member 230 may be positioned outside of (proximal to) chamber 210 with a distal end of porous body 220 positioned proximal to distal end 212 of chamber 210, or inside of chamber 210 with the distal end of porous body 220 positioned flush with distal end 212. Tube member 230 may be moved from the first position towards a second position, discussed below, to initiate deployment of porous body 220 distally from chamber 210.

As seen in FIG. 5B, distal movement (e.g., translation) of tube member 230 towards the second position may provide a corresponding movement of porous body 220, thereby causing distal portions of porous body 220 to exit chamber 210 via distal opening 213. In response to moving towards the second position, a distal portion of tube member 230 may extend into chamber 210 such that at least a portion of tube member 230 and at least a portion of porous body 220 are simultaneously positioned inside chamber 210. As porous body 220 extends distally out from chamber 210, the laterally/radially inward forces applied by chamber 210 onto an exterior of porous body 220 are gradually removed such that porous body 220 is permitted to expand. Stated differently, tube member 230 may be configured to transition porous body 220 from the compressed configuration (FIG. 4A) to the expanded configuration as porous body 220 is pushed distally out of chamber 210 when tube member 230 moves from the first position to the second position.

Figures 5C, 5D:
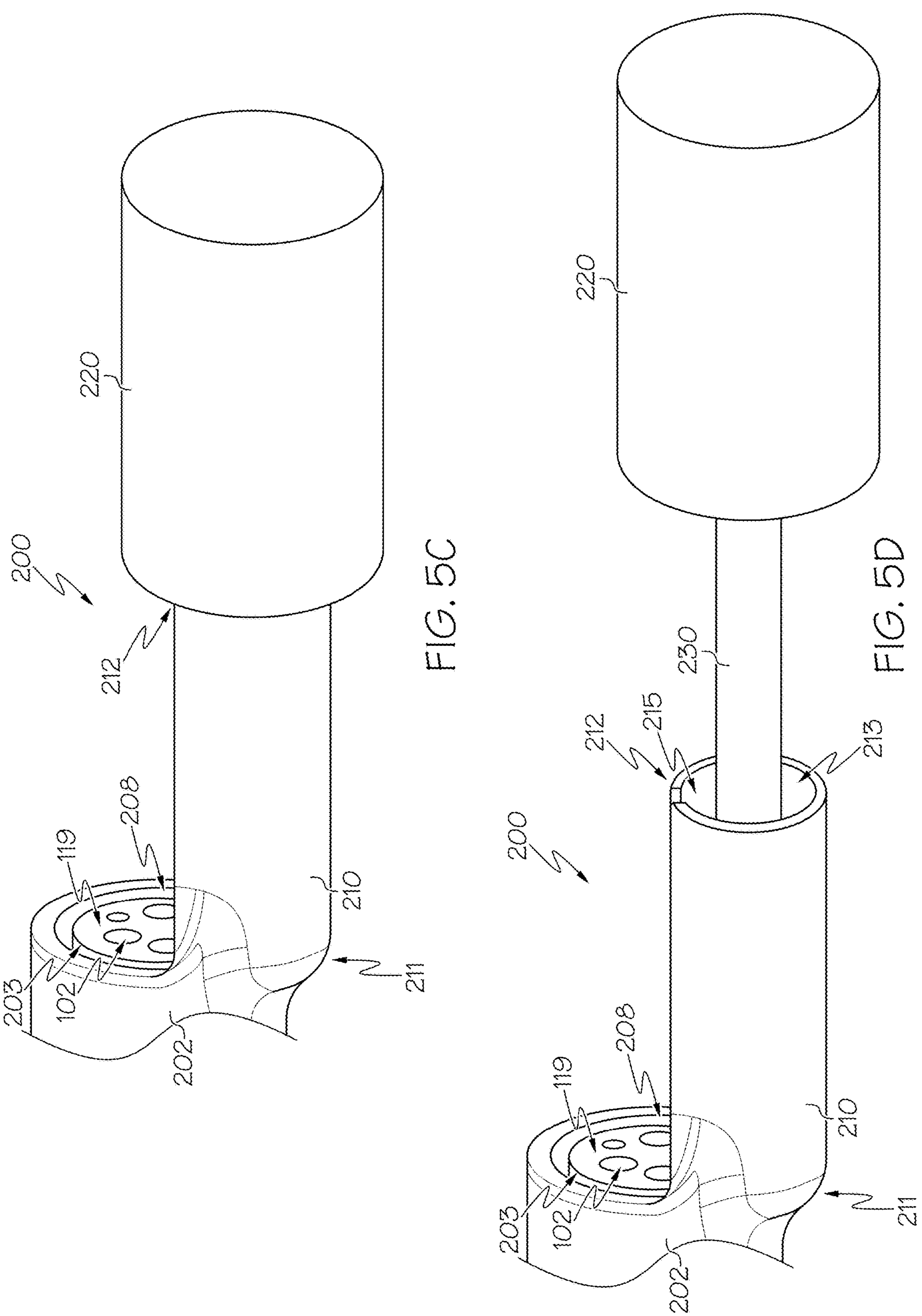
FIG. 5C shows a perspective view of the medical device of FIG. 2 in a third position, according to some embodiments.
FIG. 5D shows a perspective view of the medical device of FIG. 2 in a fourth position, according to some embodiments.

Referring now to FIG. 5C, continued distal movement of tube member 230 to a third position may cause porous body 220 to completely exit chamber 210, thereby transitioning an entirety of porous body 220 to the expanded configuration. It should be appreciated that porous body 220 may expand in a lateral/radial direction, an axial direction, and/or various other suitable manners when transitioning to the expanded configuration. In some embodiments, a position of porous body 220 may be controlled via medical system 100, and particularly by moving shaft 110. In further embodiments, a position of porous body 220 may be controlled via movement of tube member 230 relative to shaft 110, body 202, and chamber 210.

As briefly described above, tube member 230 may be fluidly coupled to a negative pressure source at a proximal end of tube member 230 (not shown) that is opposite of the terminal (distal) end of tube member 230 coupled to porous body 220. Accordingly, porous body 220 may be in fluid communication with the negative pressure source via tube member 230. As such, a negative pressure may be generated at porous body 220 via tube member 230, in response to activating the negative pressure source, to generate a suction around a surrounding environment of porous body 220, and particularly at the wound cavity.

Referring to FIG. 5D, tube member 230 may be moved to a fourth position by extending a distal end of tube member 230 further distally from working channel 120 and chamber 210 to locate porous body 220 at the wound cavity. Upon positioning porous body 220 at the wound cavity, the negative pressure source fluidly coupled to tube member 230 may be activated to apply the negative pressure to the wound cavity through porous body 220. In some aspects, fluid within a wound cavity may flow into porous body 220 and through tube member 230, for example, via capillary action, with negative pressure being applied through tube member 230. In this instance, porous body 220 may be configured to treat the wound cavity by suctioning any material (e.g., fluid) therein into the porous body 220 and through tube member 230, such as fluids from a post-surgical leak or perforation for purposes of preventing drainage and promoting healing of the wound cavity.

In other words, medical system 100 (with cap assembly 200 coupled thereto) may be operable to perform endoluminal vacuum therapy with cap assembly 200 facilitating deployment of porous body 220 (e.g., a vacuum sealed sponge) to the wound cavity for performing negative pressure wound therapy. Accordingly, cap assembly 200 (and particularly porous body 220) may help to ensure that drainage of fluid is maintained as the wound cavity decreases in size throughout the healing process. In some aspects, tube member 230 and porous body 220 may also be used to deliver fluid (e.g., saline, an antibiotic fluid, etc.) to the wound cavity, for example, to aid in the flushing and/or otherwise treating the wound cavity.

In some embodiments, tube member 230 and porous body 220 may be decoupled from body 202 and chamber 210, such as for purposes of removing shaft 110 from the subject while maintaining porous body 220 at the wound cavity. In the example, body 202 and/or chamber 210 may be formed of a material that is frangible and/or otherwise configured to at least partially deform upon an application of a predetermined force thereto, thereby releasing tube member 230 from chamber 210. Stated differently, a force exceeding a predetermined threshold may be applied to body 202 and/or chamber 210 by tube member 230, such as against an interior surface of body 202 and/or chamber 210, thereby causing body 202 and/or chamber 210 to permanently or temporarily deform for releasing tube member 230 from within chamber 210. For example, tube member 230 may be moved relatively downward until body 202 and/or chamber 210 is deformed along their respective lower surfaces such that openings are formed to allow tube member 230 to move out from body 202 and chamber 210. In this instance, shaft 110 may be removed entirely from the subject while tube member 230 and porous body 220 may be controlled independently from medical system 100.

It should be appreciated that the expanded configuration of porous body 220 may provide an increased surface area of porous body 220 in the wound cavity, which may help to allow porous body 220 to collect (e.g., absorb) more fluid from the wound cavity than a typical cylindrical sponge. Additionally, the increased surface area and increased absorbency may help to allow for medical system 100 (e.g., including porous body 220) to remain within the wound cavity for a longer period of time (i.e., with fewer removals and/or replacements).

As the wound cavity decreases in size throughout the healing process, a physician, or other user, may manually remove porous body 220 from the wound cavity for replacement with a subsequent porous body with a smaller cross-sectional dimension. In this instance, medical system 100 may be equipped with another cap assembly 200 onto shaft 110 for subsequent deployment of the smaller porous body 220 at the wound cavity. In the example, a relatively smaller porous body 220 may be continuously applied to the wound cavity via medical system 100 at regular intervals for promoting treatment of the wound. One or more of porous body 220 or tube member 230 may have antiseptic properties, for example, to help prevent or inhibit infection and/or prolong the period for which porous body 220 may remain within the wound cavity.

Figure 6:
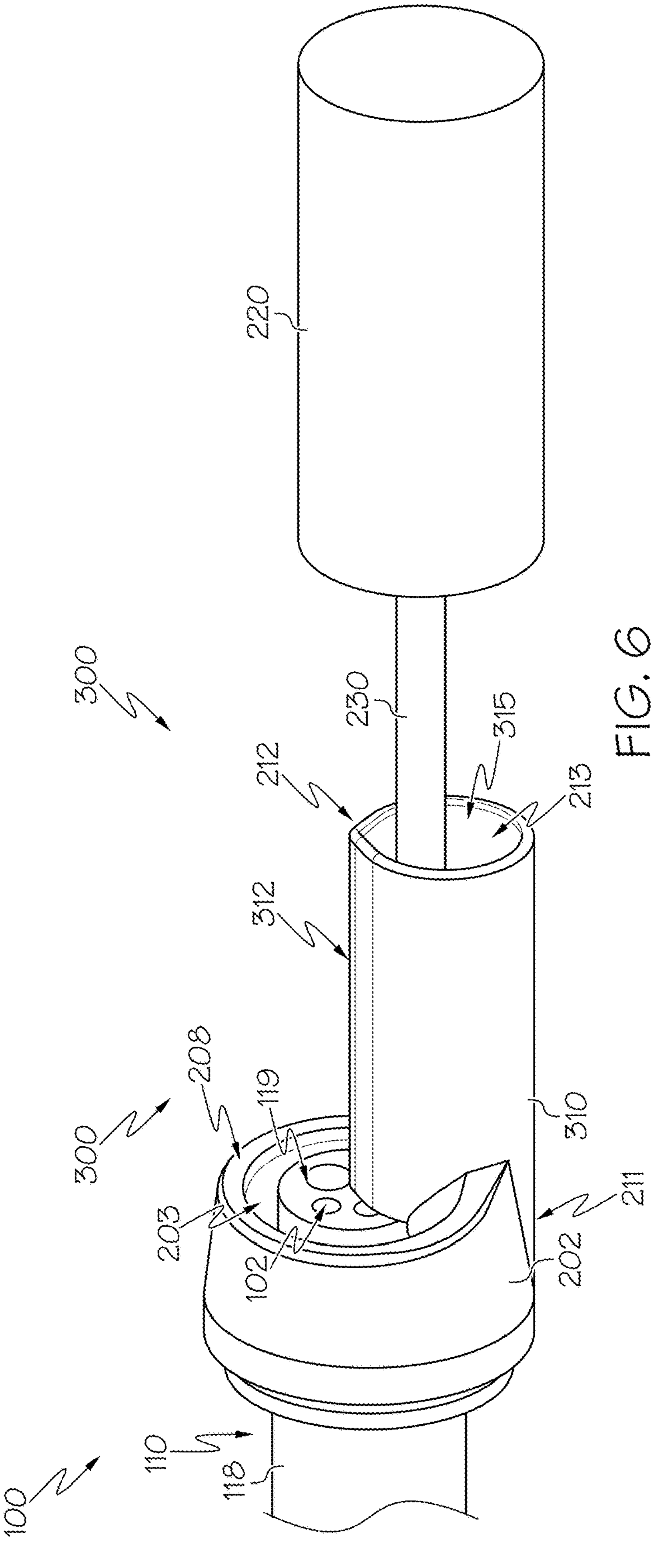
FIG. 6 shows a perspective view of another exemplary medical device coupled to the medical system of FIG. 1, according to some embodiments.
Figure 7:
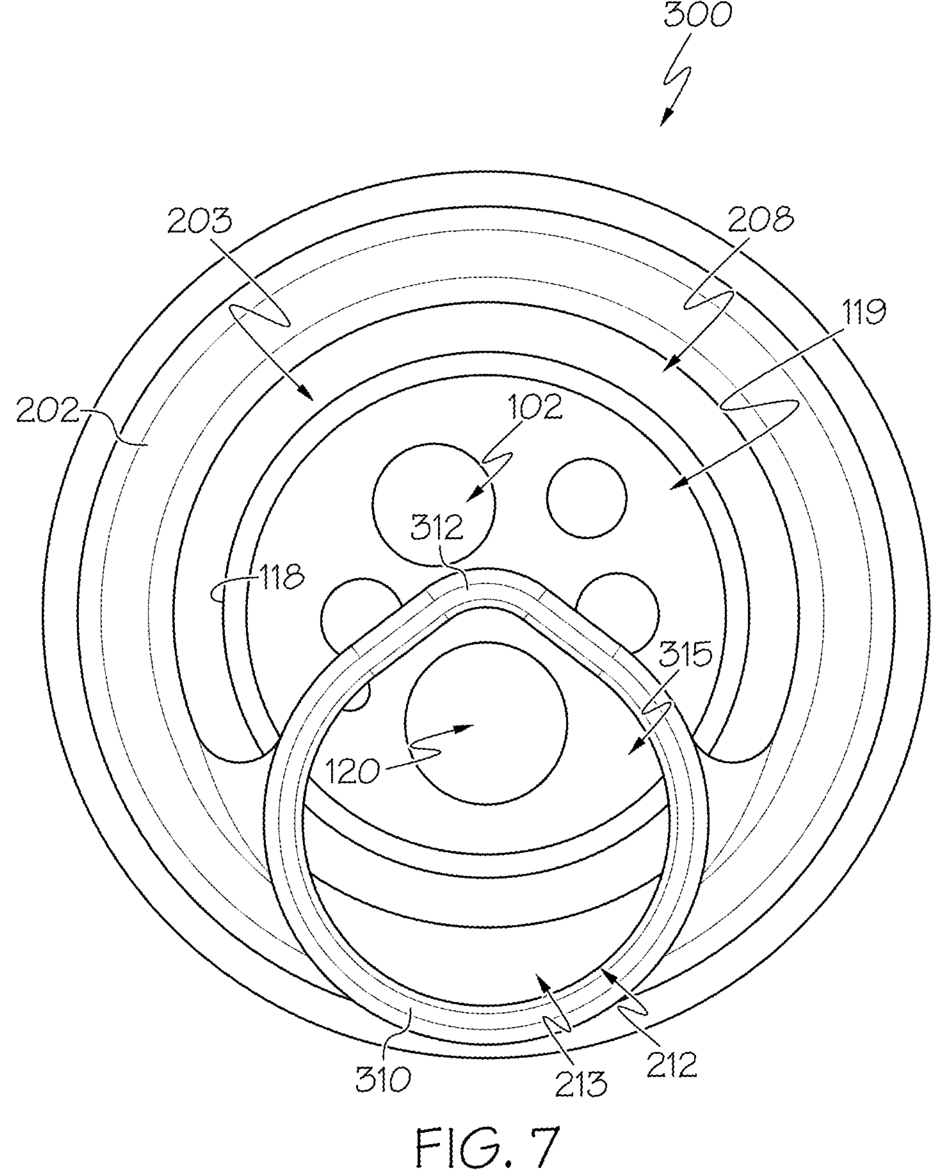
FIG. 7 shows a front elevational view of the medical device of FIG. 6 coupled to the medical system of FIG. 1, according to some embodiments.

Referring now to FIGS. 6-7, another exemplary cap assembly 300 is depicted. Cap assembly 300 may be substantially similar to cap assembly 200 except for the differences explicitly described herein. Accordingly, the same reference numerals are used to identify substantially similar components. Additionally, cap assembly 300 may be configured and operable similar to cap assembly 200. For example, similar to cap assembly 200, cap assembly 300 may include a chamber 310 having generally a cylindrical configuration that defines an interior lumen 315. Chamber 310 may include at least one extended surface and/or wall 312 (FIG. 6) formed along a portion of chamber 310 between first (proximal) end 211 and second (distal) end 212. The at least one extended wall 312 may be angled, curved, and/or otherwise extended radially outward relative to the general cylindrical configuration of the remaining portions of chamber 310. In the example, chamber 310 may form a tear-drop shape with the inclusion of extended wall 312. It should be appreciated that, in other examples, chamber 310 may be form various other suitable shapes, sizes, and/or configurations than those shown and described herein without departing from a scope of this disclosure.

Chamber 310 may be configured to receive porous body 220 in the compressed configuration as similarly shown and described above with respect to chamber 210. The at least one extended wall 312 may be sized, shaped, and/or otherwise configured to minimize an extent of compression of porous body 220 when disposed inside chamber 310. Stated differently, at least one extended wall 312 may be configured to increase a cross-sectional dimension of interior lumen 315 of chamber 310 relative to interior lumen 215 of chamber 210 (see FIG. 2), thereby defining additional space within chamber 310 for receiving porous body 220. Accordingly, chamber 310 may apply relatively less force against porous body 220 when porous body 220 is maintained inside chamber 310, thus decreasing a degree of compression of porous body 220 within chamber 210. In other words, extended wall 312 may define a cross-sectional dimension of chamber 310 that minimizes compression of porous body 220 relative to chamber 210 while maintaining maximized functionality of medical system 100 by not blocking one or more of the channels of shaft 110 when cap assembly 300 is coupled thereto.

In some embodiments, extended wall 312 may be selectively removable from a remaining portion of chamber 310 to deploy porous body 220 from cap assembly 300. For example, a pulley mechanism (not shown) may be extend through at least one of the channels of shaft 110, such as working channel 120, and secured to extended wall 312. The pulley mechanism may be configured to peel extended wall 312 off of chamber 310, thereby decoupling extended wall 312 from chamber 310, in response to actuating the pulley mechanism. The pulley mechanism may include a pull wire and/or various other suitable devices. It should be understood that the pulley mechanism may be included in cap assembly 300 in lieu of tube member 230 such that porous body 220 is not deployed from chamber 310 in response to applying a pushing force against porous body 220.

As best seen in FIG. 7, by minimizing the compressibility of porous body 220 when disposed within chamber 310, the at least one extended wall 312 may be configured to release porous body 220 from within chamber 310 and allow porous body 220 to expand upon removal of extended wall 312. The at least one extended wall 312 may be positioned relative to distal tip 119 such that the opening of working channel 120 coincides with the interior lumen of chamber 310 but one or more openings of the remaining channels of shaft 110 are not obstructed such that such channels continue to remain accessible for facilitating use of other medical tools or instruments through shaft 110 (e.g., fluid, air, lighting, etc.).

In some embodiments, tube member 230 may further include a guidewire, an outer sheath, an inner sheath, a stiffening mandrel, or other suitable devices. In one example, tube member 230 may be flexible and disposed within a rigid outer sheath (not shown) that is configured to enhance a rigidity of tube member 230 for purposes of deploying porous body 220 from chamber 310. In other words, the guidewire, outer sheath, inner sheath, and/or stiffening mandrel may be configured to inhibit tube member 230 from bending and/or kinking. For instance, tube member 230 and porous body 220 may be extended out of working channel 120 and chamber 310, respectively, and shaft 110 may be subsequently retracted from the subject. In this instance, the guidewire, outer sheath, inner sheath, stiffening mandrel, or other suitable device may be configured to push tube member 230 outward from shaft 110 and to facilitate control and/or maneuverability of tube member 230 within the subject.

In one example, the outer sheath may include a removable portion that is configured to peel and/or cut away from a remainder portion of the outer sheath to facilitate removal of tube member 230. In other examples, tube member 230 may include a guidewire and/or a stiffening mandrel (not shown) disposed therein for enhancing a rigidity of tube member 230 for purposes of deploying porous body 220 from chamber 310. In this instance, the guidewire and/or a stiffening mandrel may define a rail for facilitating movement of tube member 230 along said rail. In further examples, both tube member 230 and at least one of a guidewire and/or a stiffening mandrel may be disposed within an outer sheath. It should be appreciated that various other suitable configurations of devices may be coupled to and/or assembled with tube member 230.

In some embodiments, cap assembly 300 may be configured to selectively move (e.g., rotate) relative to distal tip 119 of shaft 110. In this instance, cap assembly 300 may be movably coupled to distal tip 119 such that an arrangement and/or orientation of body 202 may be adjusted relative to distal tip 119. By adjusting cap assembly 300 relative to shaft 110, opening 208 and chamber 310 may be repositioned to various suitable configurations relative to the one or more channels of shaft 110, and particularly the openings of said channels at distal tip 119. It should be understood that chamber 310 may remain in alignment with working channel 120 in each of such positional configurations relative to distal tip 119. Accordingly, chamber 310 (and porous body 220 received therein) may be aligned adjacent to particular channels of shaft 110, and more specifically to particular medical tools and/or instruments disposed within said channels while maintaining alignment with working channel 120, to facilitate access for said medical tools and/or instruments to porous body 220. In this instance, a relative position of chamber 310 to the distal openings of the channels at distal tip 119 may provide enhanced accessibility of porous body 220 to the one or more medical tools and/or instruments received within said channels of shaft 110 to improve control of porous body 220 during a procedure.

In some embodiments, shaft 110 may include one or more markings (e.g., arrows) along distal portion 118 and/or distal tip 119 to facilitate the various suitable arrangements of cap assembly 300. Body 202 of cap assembly 300 may similarly include corresponding markings for alignment with the markings on shaft 110 to further facilitate visual alignment of the complimentary devices.

While principles of this disclosure are described herein with reference to illustrative examples for particular applications, it should be understood that the disclosure is not limited thereto. For example, the disclosure refers to EVAC as an exemplary procedure, and the GI tract as a typical lumen for the systems and methods of the disclosure. The systems, devices, and methods of the present disclosure, however, may be used in any suitable medical procedure in any lumen or cavity within the body, for example, to aid in drainage from a wound anywhere within the body. Those having ordinary skill in the art and access to the teachings provided herein will recognize additional modifications, applications, and substitution of equivalents all fall within the scope of the examples described herein. Accordingly, the invention is not to be considered as limited by the foregoing description.

What is claimed is:

1. A medical system comprising:

a handle;

a shaft extending distally from the handle, the shaft including one or more channels extending between the handle and a distal end of the shaft, wherein at least one of the one or more channels includes a working channel;

a cap assembly coupled to the distal end of the shaft, the cap assembly including an opening that is positioned in alignment with at least one of the one or more channels at the distal end of the shaft, and a chamber that extends distally from the opening, wherein the chamber is positioned in alignment with the working channel;

a porous body movably disposed within the chamber, the porous body is configured to transition from a compressed configuration when disposed inside the chamber to an expanded configuration upon extending outwardly from the chamber; and a tube movably coupled to the cap assembly, the tube being configured to move between a first position and a second position relative to the cap assembly to transition the porous body between the compressed configuration and the expanded configuration, wherein, in the first position, a distal end of the tube is positioned outside the chamber such that the porous body is maintained inside the chamber and in the compressed configuration, and wherein, in the second position, the distal end of the tube is positioned inside the chamber such that the porous body is extended outside of the chamber and transitioned to the expanded configuration.

2. The medical system of claim 1, wherein the tube is a vacuum tube that is coupled to a negative pressure source at a proximal portion of the vacuum tube, and to the porous body at a distal portion of the vacuum tube.

3. The medical system of claim 2, wherein the vacuum tube is configured to apply negative pressure to the porous body as provided by the negative pressure source.

4. The medical system of claim 1, wherein the chamber is configured to receive the tube when the tube is in the second position, and at least a portion of the chamber is deformable to facilitate releasing the tube from the chamber.

5. The medical system of claim 1, wherein the tube is slidably received within the working channel of the shaft.

6. The medical system of claim 1, wherein the cap assembly is removably mounted on an exterior surface of the distal end of the shaft.

7. The medical system of claim 6, wherein the cap assembly is selectively rotatable about the exterior surface of the distal end of the shaft such that the chamber is repositionable relative to the one or more channels while maintaining alignment with the working channel.

8. The medical system of claim 1, wherein the porous body is a sponge, a gauze, a film, or a membrane.

9. The medical system of claim 1, wherein the chamber is at least partially transparent such that the porous body disposed inside the chamber is visible through the chamber.

10. The medical system of claim 1, wherein the chamber includes a window such that the porous body disposed inside the chamber is visible through the window by an imaging device.

11. The medical system of claim 1, wherein the chamber includes an extended wall that defines a cross-sectional dimension of the chamber that minimizes compression of the porous body received within the chamber.

12. The medical system of claim 11, wherein the extended wall is sized and shaped such that the chamber has a tear drop cross-sectional shape.

13. The medical system of claim 1, wherein the cap assembly is securely attached to the shaft via a frictional engagement between a body of the cap assembly and a distal tip of the shaft.

14. A medical device, comprising:

a cap assembly configured to be attached about a shaft of an endoscope such that a working channel of the endoscope is accessible through an opening of the cap assembly at a distal end of the shaft, the cap assembly including a chamber that extends distally from the distal end and is disposed in alignment with a working channel of the shaft; and a porous body received within the chamber, the chamber configured to compress the porous body relative to the shaft;

wherein the porous body is movable relative to the cap assembly from a first position inside the chamber and in a compressed configuration to a second position outside of the chamber and in an expanded configuration, wherein the chamber includes an extended wall that defines a cross-sectional dimension of the chamber that minimizes compression of the porous body received within the chamber.

15. The medical device of claim 14, further comprising a tube disposed inside the working channel, the tube is coupled to a negative pressure source at a first end and to the porous body at a second end, such that the negative pressure source is in fluid communication with the porous body via the tube;

wherein the tube is movable relative to the working channel to extend the porous body out from the chamber, and configured to generate a vacuum through the porous body in response to activating the negative pressure source.

16. The medical device of claim 15, wherein the chamber is configured to receive the tube when the tube extends the porous body out from the chamber, and at least a portion of the chamber is deformable to facilitate releasing the tube from the chamber.

17. The medical device of claim 14, wherein the extended wall is sized and shaped such that the chamber has a tear drop cross-sectional shape.

18. A medical system comprising:

a handle;

a shaft extending distally from the handle, the shaft including one or more channels extending between the handle and a distal end of the shaft, wherein at least one of the one or more channels includes a working channel;

a cap assembly coupled to the distal end of the shaft, the cap assembly including an opening that is positioned in alignment with at least one of the one or more channels at the distal end of the shaft, and a chamber that extends distally from the opening, wherein the chamber is positioned in alignment with the working channel; and a porous body movably disposed within the chamber, the porous body is configured to transition from a compressed configuration when disposed inside the chamber to an expanded configuration upon extending outwardly from the chamber, wherein either (1) the chamber is at least partially transparent such that the porous body disposed inside the chamber is visible through the chamber or (2) the chamber includes a window such that the porous body disposed inside the chamber is visible through the window by an imaging device.

* * * * *